(12) United States Patent
Li et al.

(10) Patent No.: US 11,510,879 B2
(45) Date of Patent: Nov. 29, 2022

(54) METAL-NUCLEIC ACID NANOPARTICLE, PREPARATION METHOD THEREFOR AND USE THEREOF

(71) Applicant: NATIONAL CENTER FOR NANOSCIENCE AND TECHNOLOGY, CHINA, Beijing (CN)

(72) Inventors: Lele Li, Beijing (CN); Congli Wang, Beijing (CN); Zhenghan Di, Beijing (CN)

(73) Assignee: NATIONAL CENTER FOR NANOSCIENCE AND TECHNOLOGY, CHINA

( * ) Notice: Subject to any disclaimer, the term of this patent is extended or adjusted under 35 U.S.C. 154(b) by 134 days.

(21) Appl. No.: 16/764,551

(22) PCT Filed: Apr. 3, 2019

(86) PCT No.: PCT/CN2019/081244
§ 371 (c)(1),
(2) Date: May 15, 2020

(87) PCT Pub. No.: WO2020/087867
PCT Pub. Date: May 7, 2020

(65) Prior Publication Data
US 2021/0378975 A1    Dec. 9, 2021

(30) Foreign Application Priority Data
Oct. 30, 2018  (CN) .......................... 201811277020.8

(51) Int. Cl.
*A61K 9/51* (2006.01)
*B82Y 5/00* (2011.01)
*B82Y 40/00* (2011.01)

(52) U.S. Cl.
CPC .......... *A61K 9/5115* (2013.01); *A61K 9/5192* (2013.01); *B82Y 5/00* (2013.01); *B82Y 40/00* (2013.01)

(58) Field of Classification Search
None
See application file for complete search history.

(56) References Cited

U.S. PATENT DOCUMENTS

| 9,617,541 | B2* | 4/2017 | Mirkin | A61P 35/00 |
|---|---|---|---|---|
| 2008/0213177 | A1* | 9/2008 | Rademacher | A61K 49/0054 424/9.1 |
| 2011/0064775 | A1* | 3/2011 | Ruiz Molina | A61K 49/0041 977/932 |
| 2016/0346204 | A1* | 12/2016 | Lin | A61P 43/00 |

FOREIGN PATENT DOCUMENTS

| CN | 102872463 | | 1/2013 |
|---|---|---|---|
| CN | 105873569 | A | 8/2016 |
| CN | 107074767 | | 8/2017 |

OTHER PUBLICATIONS

Chorny et al.; "Magnetically driven plasmid DNA delivery with biodegradable polymeric nanoparticles," 2007; FASEB; The FASEB Journal, vol. 21, pp. 2510-2519. (Year: 2007).*
Imaz et al.; "Coordination polymer particles as potential drug delivery systems," 2010, RSC; Chemical Communications, vol. 46, No. 26, pp. 7437-4739. (Year: 2010).*
Patent Cooperation Treaty (PCT), International Search Report and Written Opinion for Application PCT/CN2019/081244 filed on Apr. 3, 2019, dated Aug. 5, 2019, International Searching Authority, CN.
Li, et al. "Engineering Multifunctional DNA Hybrid Nanospheres through Coordination-Driven Self-Assembly," Angew. Chem. Int. Ed. 2019, 58, 1350-1354.
Liu, et al. "A Biomimetic Coordination Nanoplatform for Controlled Encapsulation and Delivery of Drug-Gene Combinations," Chem. Int. Ed. 2019, 131, 8896-8900.
Wnag, et al. "Coordination-driven assembly of poteins and nucleic acids in a single architecture for carrier-free intracellular co-delivery," Nano Today, 38 (2021).
Liu, et al. "Self-Assembly of Copper-DNAzyme Nanohybrids for Dual-Catalytic Tumor Therapy, " Chem. Int. Ed. 10.1002/anie. 202101744.

* cited by examiner

*Primary Examiner* — David J Blanchard
*Assistant Examiner* — Ivan A Greene
(74) *Attorney, Agent, or Firm* — McDonald Hopkins LLC (57) ABSTRACT

The present application relates to a metal-nucleic acid nanoparticle which is a nanoparticle having a spherical structure formed by assembly of metal ions with nucleic acids via coordination. The preparation thereof is mixing a metal ion solution with a nucleic acid solution to obtain a mixture followed by vortex, heating, centrifugation, washing with water and resuspension to obtain the metal-nucleic acid nanoparticles.

18 Claims, 7 Drawing Sheets

Specification includes a Sequence Listing.

METAL-NUCLEIC ACID NANOPARTICLE, PREPARATION METHOD THEREFOR AND USE THEREOF

CROSS-REFERENCE TO RELATED APPLICATION

The present application is a 35 U.S.C. 371 national stage filing of PCT Application No. PCT/CN2019/081244 filed on Apr. 3, 2019, which claims priority to a Chinese patent application No. 201811277020.8, filed on Oct. 30, 2018, disclosures of which are incorporated herein by reference in their entireties.

REFERENCE TO SEQUENCE LISTING SUBMITTED ELECTRONICALLY VIA EFS-WEB

The content of the electronically submitted sequence listing (Name: 300sequencelisting2.TXT; Size: 1,677 bytes; and Date of Creation: Aug. 31, 2020) is herein incorporated by reference in its entirety.

TECHNICAL FIELD

The present application belongs to the field of nanomaterials and relates to a metal-nucleic acid nanoparticle, and a preparation method and use thereof.

BACKGROUND

Nucleic acids are molecules that store and transmit genetic information in biological systems. The use of nucleic acids to construct nano-biomaterials and impart functionalities to them is an important milestone in the development of material assembly, which has a significant impact on nanoscience. Moreover, due to its high stability, precise controllability, and easy modification, DNA or RNA can be widely used in fields such as drug delivery and biological monitoring. Therefore, the use of DNA or RNA to construct shape-controllable nano-biomaterials and develop corresponding functions is still a research hotspot in related fields.

The sequence-specific binding property of DNA has been used to guide material assembly in nano-scale. There are two main methods for synthesizing DNA nano-structures with a controlled size and shape using DNA nano-technology. One method involves self-assemblable DNA nano-structures proposed by Seeman. Such nanostructures form DNA tiles with stable conformation through base complementation which are then assembled into a shape-controllable two-dimensional or three-dimensional structure including two-dimensional lattice, three-dimensional nanotubes and polyhedrons. These DNA-based structures have been used for gene or drug delivery and molecular sensing. The other method is first proposed by Mirkin. In this method, a non-nucleic acid-based nanoparticle is used as a template, and then a functional DNA is modified to the surface of the nanoparticle. These materials can be used for biological detection and gene therapy, etc.

CN103264165B discloses a method for synthesizing silver nanoclusters by using a single-stranded DNA as a template. This disclosure solves the problems related to the complexity and high cost in the production of nano-silver which is used for detecting mercury ions. In this method, a single-stranded DNA containing cytosine and guanine is used as a template. It is mixed with an Ag$^+$ solution, and then reduced by a reducing agent to obtain a fluorescent silver nanocluster. Such novel silver nanocluster has excellent selectivity and sensitivity, and can be used to detect Hg$^{2+}$. It is feasible for monitoring pollutants in water and has promising future.

CN101717112A discloses a method for assembling a zinc oxide nanochain by using DNA as a template, comprising the following steps: (1) mixing an aqueous solution of DNA, an aqueous solution of zinc nitrate and an aqueous solution of hexamethylenetetramine in proportion, and stirring the mixture; (2) heating the mixture to 60° C.-80° C. for 0.5-4 h; (3) cooling the mixture to a room temperature of 20° C.-25° C., and subjecting the mixture to ultrasonic treatment in an ultrasonic disperser for 10-20 min to obtain a zinc oxide nanochain assembled with DNA as the template. This method is simple, the raw materials are easy-access, the energy consumption is low, the environmental pollution is reduced, and zinc oxide nanochains with different planar shapes are constructed by manipulating the spatial structure of the biological macromolecular DNA.

CN101805022B discloses a method for preparing a barium tungstate nano-double-line array by using *Escherichia coli* genomic DNA as a template. In this method, a solution of barium nitrate is added to a solution of *Escherichia coli* genomic DNA. The mixture is mixed well and then incubated at 4-6° C., 80-90 rpm for 48-72 h. Then a solution of sodium tungstate is added. The mixture is incubated at 4-6° C., 80-90 rpm for 48-72 h. The above mixed solution is heated at 80-85° C. for 6-8 h to obtain a barium tungstate nano-double-line array with *Escherichia coli* genomic DNA as the template. This method makes it possible to use *Escherichia coli* genomic DNA as the template to synthesize a barium tungstate nano-double-line array to construct a nano-device.

Most of the above methods for preparing DNA-based nanostructures involve expensive and complicated steps. Therefore, it is necessary to develop a simple and effective method for mass production of a controllable DNA-based nanomaterial with unique functions.

SUMMARY

The following is a summary of the subject matters detailed in the present disclosure. This summary is not intended to limit the scope of the claims.

The purpose of the present application is to provide a metal-nucleic acid nanoparticle and a preparation method and use thereof.

To achieve this purpose, the present application uses the following technical solutions.

In a first aspect, the present application provides a metal-nucleic acid nanoparticle which is a nanoparticle having a spherical structure formed by combining a metal ion with a nucleic acid via coordination.

Nucleic acids are biopolymers composed of nucleotides linked together by a phosphate backbone. They have been shown to have strong coordination interaction with metal ions due to the existence of the negatively charged phosphate binding site and the nitrogen- and oxygen-containing functional groups on the base. The present application uses a coordination-directed self-assembly technique to construct a metal-nucleic acid nanostructure that not only ensures the precise controllability of the nucleic acid, but also ensures the defined particle size and shape of the entire inorganic structural unit.

In the metal-nucleic acid nanoparticle structure prepared by the present application, the metal ion is combined with the nucleic acid by coordination such that the functional nucleic acid can enter into a cell and exert its function. In addition, the metal-nucleic acid nanoparticle can carry a drug molecule or a fluorescent molecule such that the drug and the nucleic acid can exert a synergistic therapeutic effect while realizing real-time monitoring of the nanoparticle.

In the present application, the metal ion includes transition metal ions.

Optionally, the transition metal ion is any one or a combination of at least two of the group consisting of iron ions, copper ions and zinc ions.

In the present application, the nucleic acids are single-stranded DNA, double-stranded DNA, circular DNA or RNA. The RNA includes single-stranded RNA, double-stranded RNA, or circular RNA.

Optionally, the RNA is a siRNA or a mRNA.

Optionally, the metal-nucleic acid nanoparticle have a particle size of 5 to 3000 nm, such as 5 nm, 10 nm, 20 nm, 28 nm, 47 nm, 79 nm, 83 nm, 95 nm, 105 nm, 162 nm, 192 nm, 212 nm, 237 nm, 302 nm, 352 nm, 582 nm, 652 nm, 800 nm, 1000 nm, 2000 nm or 3000 nm, etc.

In a second aspect, the present application also provides a method for preparing the metal-nucleic acid nanoparticles as described above, wherein the preparation method is:

adding a metal ion solution into a nucleic acid solution to obtain a mixture, and then the mixture is subjected to vortex, heating, centrifugation, washing with water and resuspension to obtain the metal-nucleic acid nanoparticles.

In the present application, the solvent used to prepare the metal ion solution and the nucleic acid solution is deionized water.

Optionally, the vortex is carried out for 0-60 s, such as 0 s, 5 s, 10 s, 15 s, 20 s, 25 s, 30 s, 35 s, 40 s, 45 s, 50 s, 55 s or 60 s etc., optionally 10-30 s, optionally 20 s.

Optionally, the heating is carried out by metal bath heating.

Optionally, the heating is carried out at a temperature of 25-100° C., such as 25□, 30□, 40□, 50□, 60□, 75□, 80□, 901, 95□, 98□ or 1001 etc., optionally 80-100□, optionally 95□.

Optionally, the heating is carried out for 1-12 h, such as 1 h, 2 h, 3 h, 4 h, 5 h, 6 h, 7 h, 8 h, 9 h, 10 h, 11 h or 12 h etc., optionally 2-4 h, optionally 3 h.

Optionally, the centrifugation is carried out at a speed of 8000-15000 rpm, such as 8000 rpm, 9000 rpm, 9500 rpm, 10000 rpm, 11000 rpm, 12000 rpm, 13000 rpm or 14000 rpm etc., optionally 12000-14000 rpm, optionally 13000 rpm.

Optionally, the centrifugation is carried out for 1-30 min, such as 1 min, 5 min, 10 min, 12 min, 14 min, 15 min, 18 min, 20 min, 25 min or 30 min etc., optionally 5-15 min, optionally 10 min.

Optionally, the centrifugation, washing with water and resuspension are carried out for 1 to 5 times, such as 1 time, 2 times, 3 times, 4 times or 5 times, optionally 2 to 3 times.

In the present application, the concentration of the metal ion in the mixture is 0.01-30 mM, such as 0.01 mM, 0.05 mM, 0.1 mM, 0.2 mM, 0.6 mM, 1.0 mM, 2.0 mM, 3.0 mM, 5.0 mM, 10.0 mM, 20.0 mM or 30.0 mM etc.

Optionally, the concentration of the nucleic acid in the mixture is 0.005-1.0 mM, such as 0.005 mM, 0.015 mM, 0.025 mM, 0.05 mM, 0.075 mM, 0.125 mM, 0.25 mM, 0.50 mM, 0.75 mM or 1.0 mM etc.

Optionally, the molar ratio of the metal ion to the nucleic acid in the mixture is (1-100): 1, such as 1:1, 2:1, 3.8:1, 6.9:1, 14.7:1, 21.7:1, 42.6:1, 50:1, 60:1, 80:1 or 100:1 etc.

In a third aspect, the present application provides multifunctional metal-nucleic acid nanoparticle comprising the metal-nucleic acid nanoparticle as described above and an effector molecule.

The "multifunctional" in the multifunctional metal-nucleic acid nanoparticle refers to a combination of functions such as drug treatment and biological detection.

Optionally, the effector molecule is a drug molecule and/or a fluorescent tracer molecule.

Optionally, the drug is an anti-tumor drug.

Optionally, the effector molecule is used in an amount of from 1% to 60%, such as 1%, 10%, 20%, 30%, 35%, 40%, 45%, 50%, 55% or 60% etc., relative to the metal-nucleic acid nanoparticle.

In a fourth aspect, the present application provides a method for preparing a multifunctional metal-nucleic acid nanoparticle as described above, wherein the preparation method is:

adding a metal ion solution into a nucleic acid solution containing an effector molecule to obtain a mixture, and then the mixture is subjected to vortex, heating, centrifugation, washing with water and resuspension to obtain the multifunctional metal-nucleic acid nanoparticle.

As an alternative technical solution of the present application, the method for preparing the multifunctional metal-nucleic acid nanoparticle comprises the following steps:

(1) adding a metal ion solution to a nucleic acid solution containing an effector molecule such that the concentration of the metal ion is 0.01-30 mM, the concentration of the nucleic acid is 0.005-1.0 mM, and the molar ratio of the metal ion to the nucleic acid is (1-100):1;

(2) vortexing the mixture for 10-60 s, and then heating the same in a metal bath at 25-100° C. for 1-10 h;

(3) centrifuging the mixture at a speed of 8000-15000 rpm for 1-30 min and washing it with water, followed by resuspending the same mixture 1 to 5 times to obtain the multifunctional metal-nucleic acid nanoparticle.

In a fifth aspect, the present application provides use of the metal-nucleic acid nanoparticle as described above or the multifunctional metal-nucleic acid nanoparticle as described above for the preparation of a drug delivery system.

Optionally, the drug is an anti-tumor drug.

In a sixth aspect, the present application provides use of the multifunctional metal-nucleic acid nanoparticle as described above for the preparation of a biological detection reagent.

Compared with related technics, the present application has the following beneficial effects:

(1) In a metal-nucleic acid nanoparticle structure prepared by the present application, a metal ion is combined with a nucleic acid by coordination such that the functional nucleic acid can enter into a cell and exert its function. In addition, the metal-nucleic acid nanoparticle can carry a drug molecule or a fluorescent tracer molecule such that the drug and the nucleic acid can exert a synergistic therapeutic effect while realizing real-time monitoring of the nanoparticle.

(2) In the present application, the concentration and ratio of the metal ion and the nucleic acid are adjusted so that the obtained metal-nucleic acid nanoparticle has a suitable particle size which allows the metal-nucleic acid nanoparticle to recognize a tumor tissue and retain in a tumor site under enhanced permeability and retention effect of a tumor vessel, and the metal-nucleic acid nanoparticle is de-assembled in the tumor site to release the nucleic acid and drug having specific functions, thereby exerting a tumor cell-killing effect.

(3) The method for preparing a metal-nucleic acid nanoparticle provided by the present application is simple and easy, and only needs steps of mixing and stirring to obtain the metal-nucleic acid nanoparticle, and is suitable for mass production.

Other aspects will be apparent upon reading and understanding the detailed description and drawings.

DETAILED DESCRIPTION

The technical solutions of the present application are further described below by specific embodiments. It should be understood by those skilled in the art that these examples are merely to facilitate the understanding of the present application and should not be construed as limitation thereto.

Example 1

The present example provided a metal-nucleic acid nanoparticle which was a nanoparticle having a spherical structure formed by combining metal ions with nucleic acids via coordination, wherein the preparation method thereof comprised the following steps.

30 μL of 20 mM $FeCl_2.4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 20 s, and then heated in a metal bath at 95° C. for 3 h followed by centrifugation at 13,000 rpm for 10 min, washing with water and resuspension, and this washing step was carried out twice to obtain the metal-nucleic acid nanoparticles.

Example 2

The present example provided a metal-nucleic acid nanoparticle which was a nanoparticle having a spherical structure formed by combining metal ions with nucleic acids via coordination, wherein the preparation method thereof comprised the following steps.

30 μL of 20 mM $FeCl_2.4H_2O$ solution was quickly added to an aqueous solution having a total volume of 570 μL containing 150 μL of 200 μM nucleic acid, wherein the nucleic acid was a deoxyribonucleotide sequence containing 20 bases (ATCGTCGCTGCTAATCCTGA). The mixture was vortexed for 60 s, and then heated in a metal bath at 1001 for 1 h followed by centrifugation at 15000 rpm for 20 min, washing with water and resuspension, and this washing step was carried out 3 times to obtain the metal-nucleic acid nanoparticle.

Example 3

The present example provided a metal-nucleic acid nanoparticle which was a nanoparticle having a spherical structure formed by combining metal ions with a nucleic acid via coordination, wherein the preparation method thereof comprised the following steps.

75 μL of 0.2 mM $FeCl_2.4H_2O$ solution was quickly added to an aqueous solution having a total volume of 1425 μL containing 75 μL of 200 μM nucleic acid, wherein the nucleic acid was a deoxyribonucleotide sequence containing 20 bases and labeled with fluorescent dye Cy5 (TC-CATGACGTTCCTGACGTT). The mixture was vortexed for 10 s, and then heated in a metal bath at 75☐ for 1 h followed by centrifugation at 14000 rpm for 1 min, washing with water and resuspension, and this step was carried out five times to obtain the metal-nucleic acid nanoparticle.

Example 4

The present example provided a metal-nucleic acid nanoparticle which was a nanoparticle having a spherical structure formed by combining metal ions with a nucleic acid via coordination, wherein the preparation method thereof comprised the following steps.

30 μL of 50 mM $FeCl_2.4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 40 s, and then heated in a metal bath at 25☐ for 10 h followed by centrifugation at 8000 rpm for 30 min, washing with water and resuspension, and this step was carried out 1 time to obtain the metal-nucleic acid nanoparticle.

Example 5

The present example provided a metal-nucleic acid nanoparticle which was a nanoparticle having a spherical structure formed by combining metal ions with a nucleic acid via coordination, wherein the preparation method thereof comprised the following steps.

30 μL of 0.5 mM $FeCl_2.4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 60 s, and then heated in a metal bath at 25□ for 10 h followed by centrifugation at 8000 rpm for 30 min, washing with water and resuspension, and this step was carried out 1 time to obtain the metal-nucleic acid nanoparticle.

Example 6

The present example provided a metal-nucleic acid nanoparticle which was a nanoparticle having a spherical structure formed by combining metal ions with a nucleic acid via coordination, wherein the preparation method thereof comprised the following steps.

30 μL of 0.6 M $FeCl_2.4H_2O$ solution was quickly added to an aqueous solution having a total volume of 570 μL containing 75 μL of 8 mM nucleic acid, wherein the nucleic acid was a deoxyribonucleotide sequence containing 20 bases (ATCGTCGACTATAATCCTGA). The mixture was vortexed for 20 s, and then heated in a metal bath at 95° C. for 3 h followed by centrifugation at 13,000 rpm for 10 min, washing with water and resuspension, and this step was carried out twice to obtain the metal-nucleic acid nanoparticle.

Example 7

The present example provided a metal-nucleic acid nanoparticle which was a nanoparticle having a spherical structure formed by combining metal ions with a nucleic acid via coordination, wherein the preparation method thereof comprised the following steps.

75 μL of 0.2 mM $FeCl_2.4H_2O$ solution was quickly added to an aqueous solution having a total volume of 1425 μL containing 75 μL of 100 μM nucleic acid, wherein the nucleic acid was a deoxyribonucleotide sequence containing 20 bases (AAATTTTTTTTTTTTTTTTT). The mixture was vortexed for 10 s, and then heated in a metal bath at 75□ for 1 h followed by centrifugation at 14000 rpm for 1 min, washing with water and resuspension, and this step was carried out five times to obtain the metal-nucleic acid nanoparticle.

Example 8

The present example provided a metal-nucleic acid nanoparticle which was a nanoparticle having a spherical structure formed by combining metal ions with a nucleic acid via coordination, wherein the preparation method thereof comprised the following steps.

90 μL of 20 mM $FeCl_2.4H_2O$ solution was quickly added to an aqueous solution having a total volume of 570 μL containing 225 μL of 200 μM nucleic acid, wherein the nucleic acid was a deoxyribonucleotide sequence containing 20 bases (TCCATGACGTTCCTGACGTT). The mixture was vortexed for 20 s, and then heated in a metal bath at 95° C. for 3 h followed by centrifugation at 13,000 rpm for 10 min, washing with water and resuspension, and this step was carried out twice to obtain the metal-nucleic acid nanoparticle.

Example 9

The present example provided a metal-nucleic acid nanoparticle which was a nanoparticle having a spherical structure formed by combining metal ions with a nucleic acid via coordination, wherein the preparation method thereof comprised the following steps.

30 μL of 20 mM $FeCl_2.4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 20 s, and then heated in a metal bath at 75□ for 3 h followed by centrifugation at 13,000 rpm for 10 min, washing with water and resuspension, and this step was carried out twice to obtain the metal-nucleic acid nanoparticle.

Example 10

The present example provided a metal-nucleic acid nanoparticle which was a nanoparticle having a spherical structure formed by combining metal ions with a nucleic acid via coordination, wherein the preparation method thereof comprised the following steps.

30 μL of 20 mM $FeCl_2.4H_2O$ solution was quickly added to an aqueous solution having a total volume of 570 μL containing 75 μL of 200 μM nucleic acid, wherein the nucleic acid was a ribonucleotide sequence small interfering RNA containing 21 bases (GCGGCAGCAGGUAGCAAAGdTdT). The mixture was vortexed for 20 s, and then heated in a metal bath at 95° C. for 3 h followed by centrifugation at 13,000 rpm for 10 min, washing with water and resuspension, and this step was carried out twice to obtain the metal-nucleic acid nanoparticle.

Example 11

The present example provided a metal-nucleic acid nanoparticle which was a nanoparticle having a spherical structure formed by combining metal ions with a nucleic acid via coordination, wherein the preparation method thereof comprised the following steps.

30 μL of 20 mM $FeCl_2.4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 20 s, and then heated in a metal bath at 50□ for 3 h followed by centrifugation at 13,000 rpm for 10 min, washing with water and resuspension, and this step was carried out twice to obtain the metal-nucleic acid nanoparticle.

Example 12

The present example provided a metal-nucleic acid nanoparticle which was a nanoparticle having a spherical structure formed by combining metal ions with a nucleic acid via coordination, wherein the preparation method thereof comprised the following steps.

30 μL of 20 mM $FeCl_2.4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 40 s, and then heated in a metal bath at 95□ for 3 h followed by centrifugation at 13,000 rpm for 10 min, washing with water and resuspension, and this step was carried out twice to obtain the metal-nucleic acid nanoparticle.

Example 13

The present example provided a metal-nucleic acid nanoparticle which was a nanoparticle having a spherical structure formed by combining metal ions with a nucleic acid via coordination, wherein the preparation method thereof comprised the following steps.

30 μL of 20 mM $FeCl_2 \cdot 4H_2O$ solution was quickly added to an aqueous solution having a total volume of 570 μL containing 75 μL of 200 μM nucleic acid, wherein the nucleic acid was a deoxyribonucleotide sequence containing 20 bases (ATCGTCGATGCTAATCCTGA). The mixture was vortexed for 20 s, and then heated in a metal bath at 95° C. for 3 h followed by centrifugation at 13,000 rpm for 15 min, washing with water and resuspension, and this step was carried out twice to obtain the metal-nucleic acid nanoparticle.

Example 14

The present example provided a drug-loaded metal-nucleic acid nanoparticle which was a nanoparticle having a spherical structure formed by combining metal ions with a nucleic acid via coordination and loaded with a drug, wherein the preparation method thereof comprised the following steps.

18 μL of 20 mM $FeCl_2 \cdot 4H_2O$ solution was quickly added to an aqueous solution having a total volume of 582 μL containing 45 μL of 200 μM nucleic acid and 150 μL of 1 mg/mL ribonuclease, wherein the nucleic acid was a deoxyribonucleotide sequence containing 20 bases (ATCGTCGATGCTAATCCTGA). The mixture was vortexed for 20 s, and then heated in a metal bath at 60□ for 3 h followed by centrifugation at 13,000 rpm for 10 min, washing with water and resuspension, and this step was carried out twice to obtain the drug-loaded metal-nucleic acid nanoparticle.

Example 15

The present example provided a drug-loaded metal-nucleic acid nanoparticle which was a nanoparticle having a spherical structure formed by combining metal ions with a nucleic acid via coordination and loaded with a drug, wherein the preparation method thereof comprised the following steps.

30 μL of 20 mM $FeCl_2 \cdot 4H_2O$ solution was quickly added to an aqueous solution having a total volume of 570 μL containing 75 μL of 200 μM nucleic acid and 190 μL of 1 mg/mL ribonuclease, wherein the nucleic acid was a deoxyribonucleotide sequence containing 20 bases (ATCGTCGATGCTAATCCTGA). The mixture was vortexed for 40 s, and then heated in a metal bath at 95□ for 3 h followed by centrifugation at 13,000 rpm for 10 min, washing with water and resuspension, and this step was carried out twice to obtain the drug-loaded metal-nucleic acid nanoparticle.

Example 16

The present example provided a drug-loaded metal-nucleic acid nanoparticle which was a nanoparticle having a spherical structure formed by combining metal ions with a nucleic acid via coordination and loaded with a drug, wherein the preparation method thereof comprised the following steps.

30 μL of 20 mM $FeCl_2 \cdot 4H_2O$ solution was quickly added to an aqueous solution having a total volume of 570 μL containing 150 μL of 200 μM nucleic acid and 300 μL of 1 mg/mL ribonuclease, wherein the nucleic acid was a deoxyribonucleotide sequence containing 20 bases (ATCGAAAATGCTAATCCTGA). The mixture was vortexed for 20 s, and then heated in a metal bath at 80□ for 3 h, followed by centrifugation at 13,000 rpm for 15 min, washing with water and resuspension, and this step was carried out twice to obtain the drug-loaded metal-nucleic acid nanoparticle.

Example 17

The present example provided a drug-loaded metal-nucleic acid nanoparticle which was a spherical nanoparticle having a spherical structure formed by combining metal ions with a nucleic acid via coordination and loaded with a drug, wherein the preparation method thereof comprised the following steps.

30 μL of 20 mM $FeCl_2 \cdot 4H_2O$ solution was quickly added to an aqueous solution having a total volume of 570 μL containing 75 μL of 200 μM nucleic acid and 10 μL of 10 mM doxorubicin, wherein the nucleic acid was a deoxyribonucleotide sequence containing 20 bases (ATCGTCGATGCTAATCCTGA). The mixture was vortexed for 20 s, and then heated in a metal bath at 95° C. for 3 h followed by centrifugation at 13,000 rpm for 10 min, washing with water and resuspension, and this step was carried out twice to obtain the drug-loaded metal-nucleic acid nanoparticle.

Example 18

Test on Morphology and Particle Size:

The products prepared in Examples 1-17 were tested for morphology and particle size. The specific operation method was as follows. The prepared product was ultrasonically dispersed with deionized water, and the dispersion was dropped on a copper mesh. After it was naturally dried, the sample was observed for morphology with a transmission electron microscope. Then an average particle size of any 100 particles in the electron micrograph was statistically calculated using ImageJ software and was deemed as an average particle size of the sample. The results are shown in FIG. 1 and Table 1. FIGS. 1A, 1B, 1C, 1D, and 1E are electron micrographs of Example 2, Example 3, Example 6, Example 10, and Example 14, respectively.

As can be seen from FIGS. 1A to 1E, the prepared products were nanoparticles having a spherical structure.

TABLE 1

| Product | Particle size |
|---|---|
| Example 1 | 75 nm |
| Example 2 | 100 nm |
| Example 3 | 150 nm |
| Example 4 | 320 nm |
| Example 5 | 330 nm |
| Example 6 | 520 nm |
| Example 7 | 20 nm |
| Example 8 | 200 nm |
| Example 9 | 815 nm |
| Example 10 | 110 nm |
| Example 11 | 765 nm |
| Example 12 | 720 nm |

TABLE 1-continued

| Product | Particle size |
| --- | --- |
| Example 13 | 660 nm |
| Example 14 | 1.5 μm |
| Example 15 | 2.1 μm |
| Example 16 | 2.7 μm |
| Example 17 | 270 nm |

Example 19

Test on UV Performance

The product prepared in Example 1 was tested for UV performance. The specific operation method was as follows. The sample was formulated into dispersions having the same concentration. The dispersion was placed in a cuvette and measured for UV absorption within the spectral range of 250-600 nm with an UV-visible spectrophotometer. The position of an ultraviolet absorption peak with maximum peak intensity was the ultraviolet absorption wavelength of the product. The results are shown in FIG. 2.

Figure 1A:
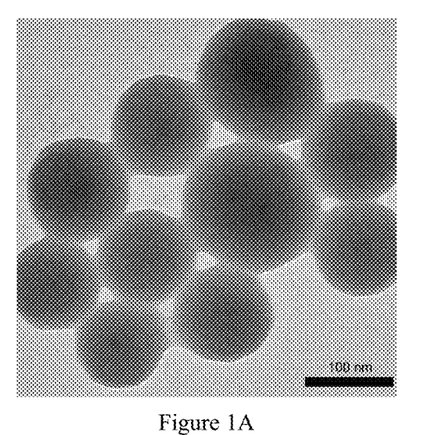
FIG. 1A is a transmission electron micrograph of the metal-nucleic acid nanoparticles prepared in Example 2.
Figure 1B:
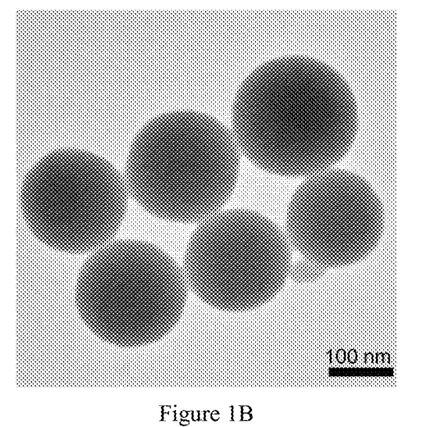
FIG. 1B is a transmission electron micrograph of the metal-nucleic acid nanoparticles prepared in Example 3.
Figure 1C:
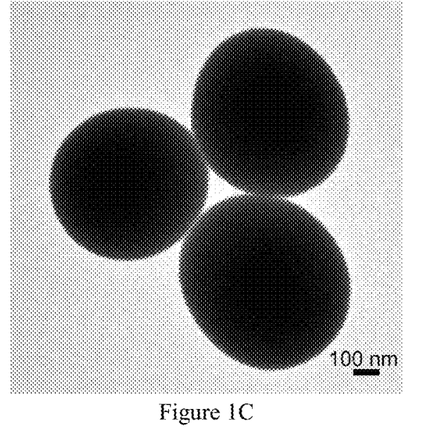
FIG. 1C is a transmission electron micrograph of the metal-nucleic acid nanoparticles prepared in Example 6.
Figure 1D:
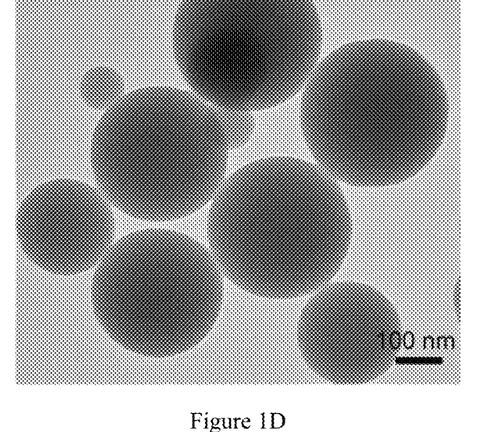
FIG. 1D is a transmission electron micrograph of the metal-nucleic acid nanoparticles prepared in Example 10.
Figure 1E:
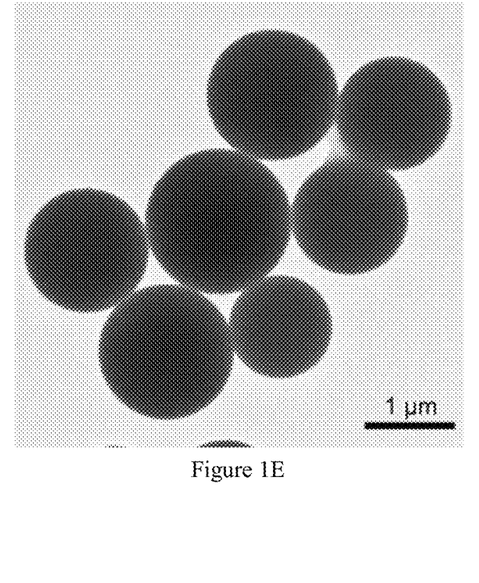
FIG. 1E is a transmission electron micrograph of the metal-nucleic acid nanoparticles prepared in Example 14.
Figure 2:
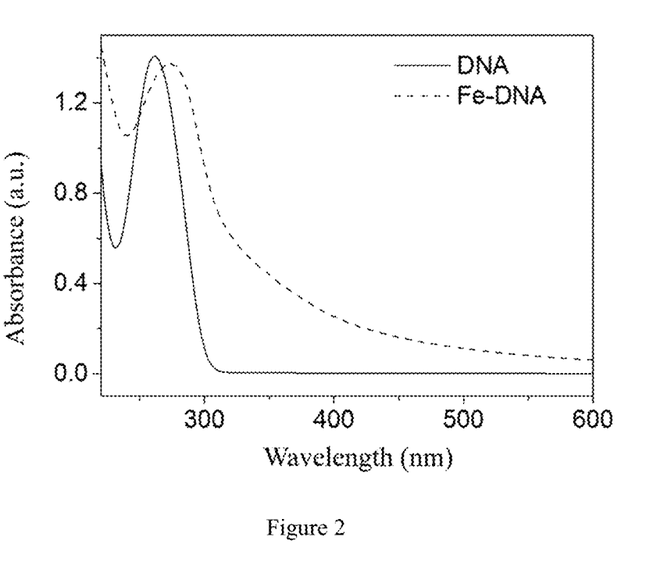
FIG. 2 is a graph showing the ultraviolet spectrum of the metal-nucleic acid nanoparticles prepared in Example 1.

It can be seen from FIG. 2 that the nanoparticle prepared in Example 1 had an ultraviolet absorption peak near 272 nm, which was red-shifted by about 10 nm compared with the ultraviolet spectrum of pure DNA. The red shift effect was related to the coordination of metal ions with DNA.

Example 20

Test on Nanoparticle Crystal Form:

The product prepared in the Example 1 was tested for nanoparticle crystal form. The specific operation method was as follows. The sample was dispersed with deionized water, and the dispersion was dropped on a copper mesh. After it was naturally dried, the sample was observed for morphology with a high-resolution transmission electron microscope. Electron diffraction was used to perform selected area electron diffraction to analyze whether the sample was crystalline. The results are shown in FIGS. 3A and 3B.

Figure 3A:
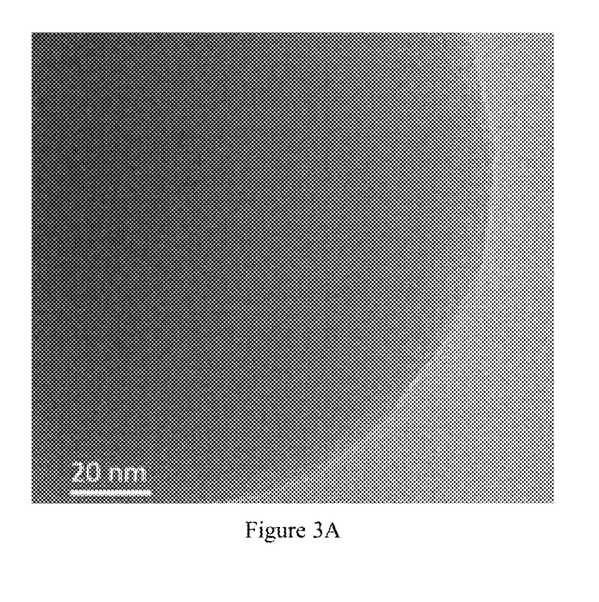
FIG. 3A is a high-resolution transmission electron micrograph of the metal-nucleic acid nanoparticles prepared in Example 1.
Figure 3B:
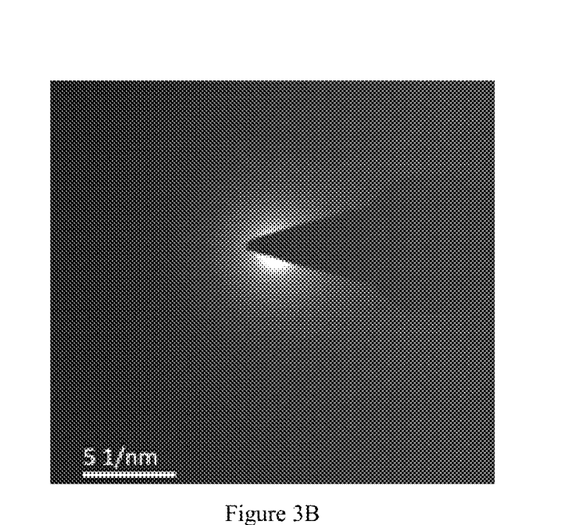
FIG. 3B is a diagram showing the selected area electron diffraction analysis of the metal-nucleic acid nanoparticle prepared in Example 1.

As can be seen from FIGS. 3A and 3B, the high-resolution transmission electron micrograph showed that the nanoparticle prepared in Example 1 had no lattice fringes, and the selected area electron diffraction diagram showed no diffraction spots, indicating that the nanoparticle has an amorphous structure.

Example 21

Test on Element Distribution:

The product prepared in Example 1 was tested for element distribution. The specific operation method was as follows. The sample was dispersed with deionized water, and the dispersion was dropped on a copper mesh. After it was naturally dried, the elemental distribution was analyzed and linear scanning was performed with high-angle annular dark-field scanning transmission electron microscopy-energy dispersive X-ray spectrometer. The results are shown in FIGS. 4A and 4B.

Figure 4A:
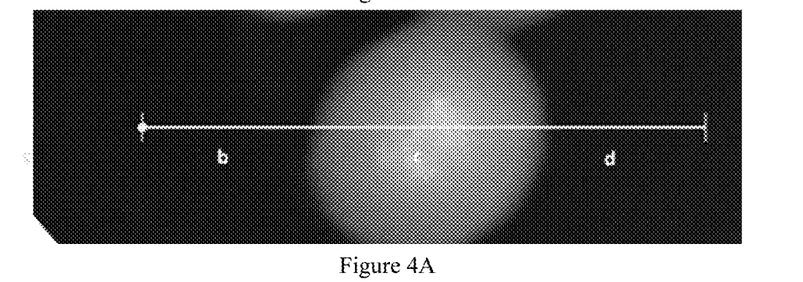
FIG. 4A is a schematic diagram showing the selected area in the linear scanning of the metal-nucleic acid nanoparticle prepared in Example 1.
Figure 4B:
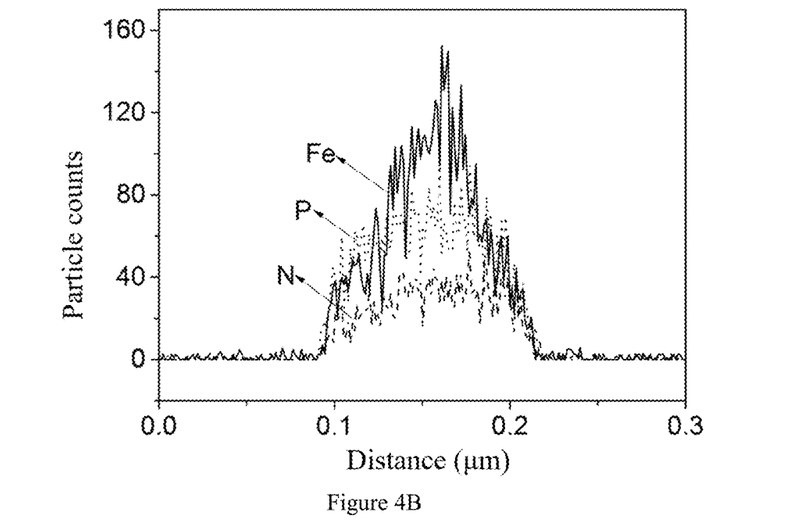
FIG. 4B is a graph showing the linear scanning of the selected area of FIG. 4A.

As can be seen from FIGS. 4A and 4B, elements Fe, P and N were uniformly distributed throughout the nanoparticle, indicating that Fe and DNA were well assembled together.

Example 22

Test on Infrared Spectrum:

The product prepared in Example 1 was tested for infrared spectrum. The specific operation method was as follows. The sample was dispersed with deionized water, and the obtained dispersion was dropped on a silicon wafer. After it was naturally dried, functional groups in the sample were analyzed with a Fourier transform infrared spectrometer. The result is shown in FIG. 5.

Figure 5:
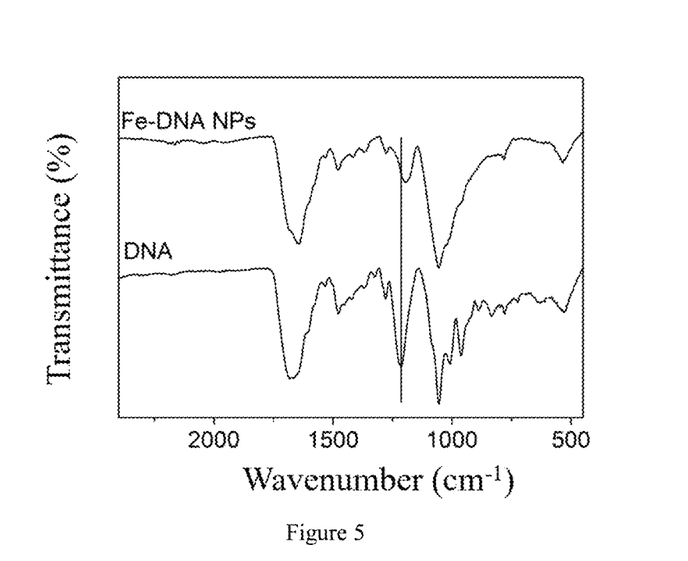
FIG. 5 is a graph showing the infrared spectrum of the metal-nucleic acid nanoparticle prepared in Example 1.

It can be seen from FIG. 5 that the peak of the phosphate skeleton in the DNA was at 1213 $cm^{-1}$, while the peak of the phosphate skeleton in the metal-DNA nanoparticle was shifted to 1192 $cm^{-1}$, indicating that the phosphate skeleton had a coordination effect.

Example 23

Test on Potential:

The product prepared in Example 1 was tested for potential. The specific operation method was as follows. The sample was dispersed with deionized water, diluted and placed in a dish for potential measurement and tested with a nano-laser particle size analyzer. The result is shown in FIG. 6.

Figure 6:
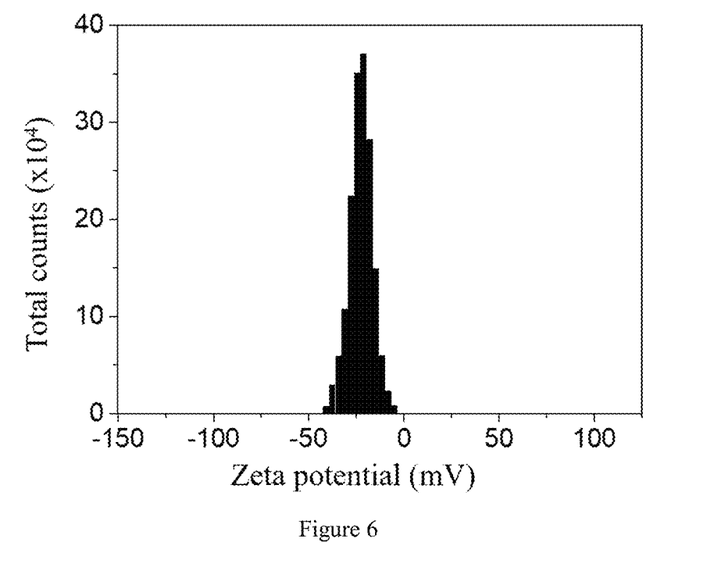
FIG. 6 is a graph showing the Zeta potential of the metal-nucleic acid nanoparticles prepared in Example 1.

As can be seen from FIG. 6, the potential of the nanoparticles was −22.5 mV, indicating that the DNA was combined with Fe to make it uniformly disperse in the aqueous solution.

Example 24

Flow Cytometry Test:

The product prepared in Example 3 was subjected to a flow cytometry test. The specific operation method was as follows. RAW264.7 macrophages were cultured in Dulbecco's modified Eagle medium (DMEM) supplemented with 100 units/ml water-soluble penicillin G, 4.5 mg/mL glucose, $4\times10^{-3}$ M L-glutamine, 10% FBS and 100 μg/mL streptomycin at a culture density of $4\times10^5$ cells/well in a culture dish in a $CO_2$ incubator at 37° C. After 24 hours of incubation, the medium was washed, and fresh cell culture medium containing the product of Example 3 was added. After an additional 4 hours of incubation, the treated cells were rinsed with pre-heated PBS solution (3×2 mL) to remove free nanoparticles, and fresh medium was added to the culture dish. An appropriate number of cells was taken and treated with an antibody, and then subjected to the flow cytometry test using a flow cytometer. The result is shown in FIG. 7.

Figure 7:
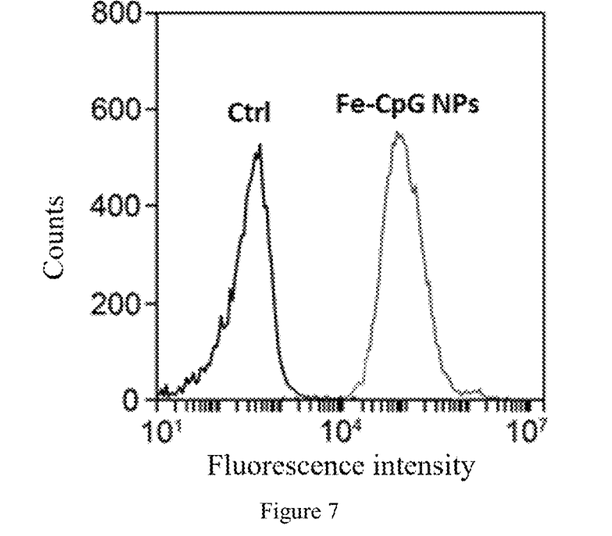
FIG. 7 is a graph showing the results of the flow cytometry assay of cellular uptake of the metal-nucleic acid nanoparticles prepared in Example 3.

As can be seen from FIG. 7, the nanoparticles prepared in Example 3 showed strong fluorescence intensity, quantitatively indicating that the nanoparticles entered into the cells well.

Example 25

Figure 8A:
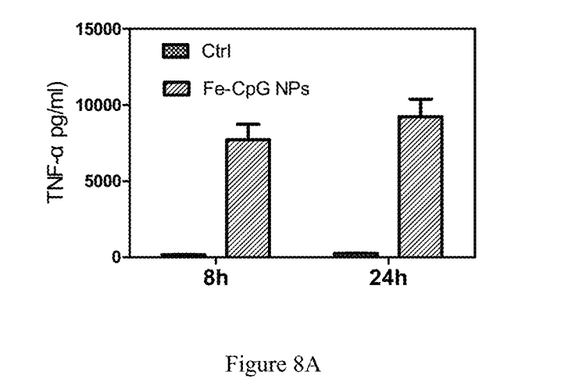
FIG. 8A is a graph showing the results of an ELISA test of the immune factor TNF-α.

ELISA Test:

The product prepared in Example 3 was subjected to an ELISA test. The specific operation method was as follows. RAW264.7 macrophages were cultured in Dulbecco's modified Eagle medium (DMEM) supplemented with 100 units/ml water-soluble penicillin G, 4.5 mg/mL glucose, $4\times10^{-3}$ M L-glutamine, 10% FBS and 100 μg/mL streptomycin at a culture density of $4\times10^5$ cells/well in a culture dish in a $CO_2$ incubator at 37° C. After 24 hours of incubation, the medium was washed, and fresh cell culture medium containing the product of Example 3 was added. After an additional 4 hours of incubation, the treated cells were rinsed with pre-heated PBS solution (3×2 mL) to remove free nanoparticles, and fresh medium was added to the culture dish. An appropriate number of cells was taken and treated with an antibody, and then subjected to the ELISA test using a microplate reader. The result is shown in FIG. 8. FIG. 8A shows the detection results of TNF-α factor, and FIG. 8B shows the detection results of IL-6 factor.

Figure 8B:
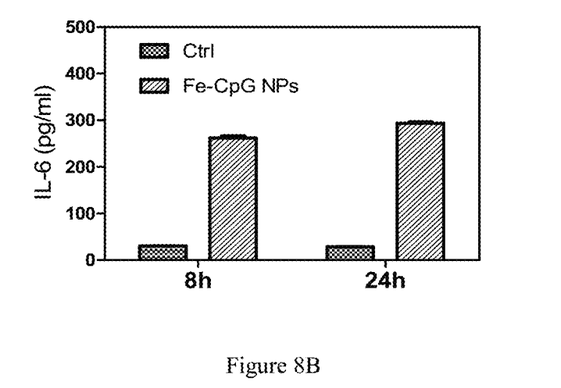
FIG. 8B is a graph showing the results of an ELISA test of the immune factor IL-6.

As can be seen from FIGS. 8A and 8B, the nanoparticles prepared in Example 3 produced a large amount of immune factors TNF-α and IL-6, which can kill tumor cells by immune response (in the figures, Ctrl represented a control group and Fe-CpG NPs represented the nanoparticles prepared in Example 3.)

Example 26

MTT Test:

The product prepared in Example 17 was subjected to MTT test. The specific operation method was as follows. RAW264.7 macrophages were cultured in Dulbecco's modified Eagle medium (DMEM) supplemented with 100 units/ml water-soluble penicillin G, 4.5 mg/mL glucose, $4 \times 10^{-3}$ M L-glutamine, 10% FBS and 100 μg/mL streptomycin at a culture density of $4 \times 10^5$ cells/well in a culture dish in a $CO_2$ incubator at 37° C. After 24 hours of incubation, the medium was washed, and fresh cell culture medium containing the product of Example 17 was added. After an additional 4 hours of incubation, the treated cells were rinsed with pre-heated PBS solution (3×2 mL) to remove free nanoparticles, and fresh medium was added to the culture dish. An appropriate number of cells were taken and treated, and then medium containing MTT was added. The cells were subjected to the MTT test using a microplate reader. The result is shown in FIG. 9.

Figure 9:
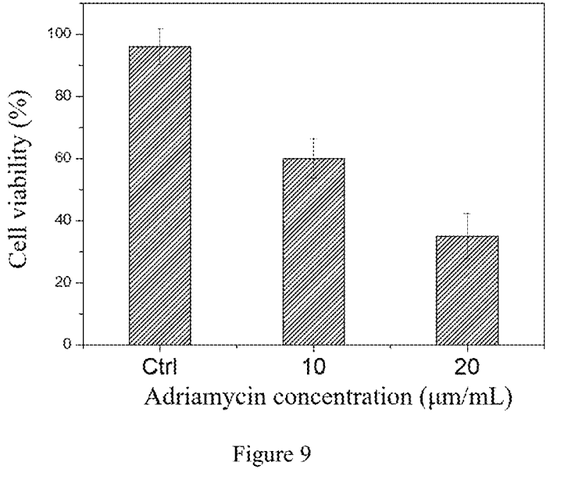
FIG. 9 is a graph showing the results of an MTT assay of the drug-loaded metal-nucleic acid nanoparticle prepared in Example 17.

As can be seen from FIG. 9, the cells incubated with the doxorubicin co-encapsulated metal-DNA nanoparticles prepared in Example 17 induced a low cell viability, indicating that the nanoparticles had a strong killing effect on tumor cells (Ctrl in the figure represented a control group).

The applicant states that the present application describes the metal-nucleic acid nanoparticle of the present application and the preparation method and use thereof by the above examples. However, the present application is not limited to the above examples, and it does not mean that the present application must rely on the above examples to implement.

The foregoing describes the optional embodiments of the present application in detail. However, the present application is not limited to the specific details in the foregoing embodiments, and various simple modifications may be made to the technical solutions of the present application within the technical concept of the present application.

In addition, it should be noted that the specific technical features described in the above specific embodiments may be combined in any suitable manner without contradiction. In order to avoid unnecessary repetition, the present application will not further explain the various possible combinations.

What is claimed is:

1. A metal ion-nucleic acid nanoparticle, wherein the metal ion-nucleic acid nanoparticle is a nanoparticle having a spherical structure formed by assembly of metal ions with nucleic acids via coordination interaction, wherein the metal ions are Fe(II) ions.

2. The metal ion-nucleic acid nanoparticles according to claim 1, wherein the metal ion-nucleic acid nanoparticle has a particle size of 5 to 3000 nm.

3. A preparation method for the metal ion-nucleic acid nanoparticle according to claim 1, wherein the preparation method is: mixing an Fe(II) ion solution with a nucleic acid solution to obtain a mixture followed by vortex, heating, centrifugation, washing with water and resuspension to obtain the metal ion-nucleic acid nanoparticles.

4. The preparation method according to claim 3, wherein a concentration of the Fe(II) ion in the mixture is 0.01-30 mM; a concentration of the nucleic acid in the mixture is 0.005-1.0 mM.

5. The preparation method according to claim 3, wherein a molar ratio of the Fe(II) ion to the nucleic acid in the mixture is (1-100): 1.

6. The preparation method according to claim 3, wherein a solvent used to prepare the Fe(II) ion solution and the nucleic acid solution is deionized water; the vortex is carried out for 0-60 s—the heating is carried out by metal bath heating; the heating is carried out at a temperature of 25-100° C., the heating is carried out for 1-10 h; the centrifugation is carried out at a speed of 8000-15000 rpm, the centrifugation is carried out for 1-30 min—the centrifugation, washing with water and resuspension are carried out for 1 to 5 times.

7. A multifunctional metal ion-nucleic acid nanoparticle, wherein the multifunctional metal ion-nucleic acid nanoparticle comprises the metal ion-nucleic acid nanoparticle according to claim 1 and an effector molecule.

8. The multifunctional metal ion-nucleic acid nanoparticle according to claim 7, wherein the effector molecule is a drug molecule and/or a fluorescent tracer molecule.

9. The multifunctional metal ion-nucleic acid nanoparticle according to claim 7, wherein the effector molecule is used in an amount of ranges from 1% to 60% relative to the metal ion-nucleic acid nanoparticle.

10. A preparation method for the multifunctional metal ion-nucleic acid nanoparticle according to claim 7, wherein the preparation method is: adding an Fe(II) metal ion solution into a nucleic acid solution containing an effector molecule to obtain a mixture followed by vortex, heating, centrifugation, washing with water and resuspension to obtain the multifunctional metal ion-nucleic acid nanoparticles.

11. The preparation method according to claim 10, wherein the preparation method comprises the following steps: (1) adding an Fe(II) ion solution to a nucleic acid solution containing an effector molecule such that a concentration of the Fe(II) ion is 0.01-30 mM, a concentration of the nucleic acid is 0.005-1.0 mM, and a molar ratio of the Fe(II) ion to the nucleic acid is (1-100):1; (2) vortexing the mixture for 0-60 s, and then heating the same in a metal bath at 25-100 C for 1-10 h; (3) centrifuging the mixture at a speed of 8000-15000 rpm for 1-30 min, washing it with water and resuspending the same 1 to 5 times to obtain the multifunctional metal ion-nucleic acid nanoparticle.

12. A drug delivery system comprising the metal ion-nucleic acid nanoparticle according to claim 1.

13. The drug delivery system according to claim 12, wherein the drug is an anti-tumor drug.

14. A biological detection reagent comprising the multifunctional metal ion-nucleic acid nanoparticle according to claim 7.

15. The metal ion-nucleic acid nanoparticle according to claim 2, the nucleic acid is a single-stranded DNA, a double-stranded DNA, a circular DNA, an RNA, or a combination of them.

16. The metal ion-nucleic acid nanoparticle according to claim 15, wherein the RNA is a siRNA or a miRNA.

17. The multifunctional metal ion-nucleic acid nanoparticle according to claim 8, the drug is an anti-tumor drug.

18. A drug delivery system comprising the multifunctional metal ion-nucleic acid nanoparticle according to claim 7, wherein the drug is an anti-tumor drug.

\* \* \* \* \*

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
atcgtcgctg ctaatcctga                                           20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
tccatgacgt tcctgacgtt                                           20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
atcgtcgatg ctaatcctga                                           20

<210> SEQ ID NO 4
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 4
atcgtcgact ataatcctga                                              20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
aaattttttt tttttttttt                                              20

<210> SEQ ID NO 6
<211> LENGTH: 21
<212> TYPE: RNA
<213> ORGANISM: Artificial Sequence
<220> FEATURE:
<223> OTHER INFORMATION: synthetic oligonucleotide, wherein t represents
      dt

<400> SEQUENCE: 6
gcggcagcag guagcaaagtt                                             21

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
atcgaaaatg ctaatcctga                                              20
```